United States Patent [19]

Buttazzoni et al.

[11] Patent Number: 4,705,694
[45] Date of Patent: Nov. 10, 1987

[54] PROCESS FOR MAKING BIOACTIVE COATINGS ON OSSEOUS PROSTHESES, AND PROSTHESES THUS OBTAINED

[75] Inventors: Bernard Buttazzoni, Marseille; Philippe Leseur, La Rochelle; Jacques Thebault, Bordeaux, all of France, Georges Constant, deceased, late of Ramonville Saint-Agne, France, by Marie-Josette Constant, Francoise Constant, Philippe Constant, executors

[73] Assignee: Societe Europeenne de Propulsion, Puteaux, France

[21] Appl. No.: 929,716

[22] Filed: Nov. 12, 1986

Related U.S. Application Data

[63] Continuation-in-part of Ser. No. 626,901, Jul. 2, 1984, abandoned.

[30] Foreign Application Priority Data

Jul. 1, 1983 [FR] France ................................ 83 11026

[51] Int. Cl.⁴ .......................... A61C 13/30; A61F 1/24
[52] U.S. Cl. ............................................ 427/2; 623/16
[58] Field of Search ................................ 427/2; 623/16

[56] References Cited

U.S. PATENT DOCUMENTS 4,366,183 12/1982 Ghemmidh et al. ..................... 427/2

Primary Examiner—Michael R. Lusignan
Attorney, Agent, or Firm—Schwartz, Jeffery, Schwaab, Mack, Blumenthal & Evans

[57] ABSTRACT

The present invention relates to a process for making bioactive coatings on osseous prostheses, wherein a mist of particles containing calcium ions and orthophosphate ions is made from solutions and said mist is brought into contact with a substrate (notably an implant) made of inert material under such operational conditions that a hydroxyapatite coating is formed by reaction on the hot surface of said inert substrate, said process being characterized by the fact that the operating conditions to make the deposit are selected so that a liquid film forms on the hot surface of said substrate during the deposition.

1 Claim, 1 Drawing Figure

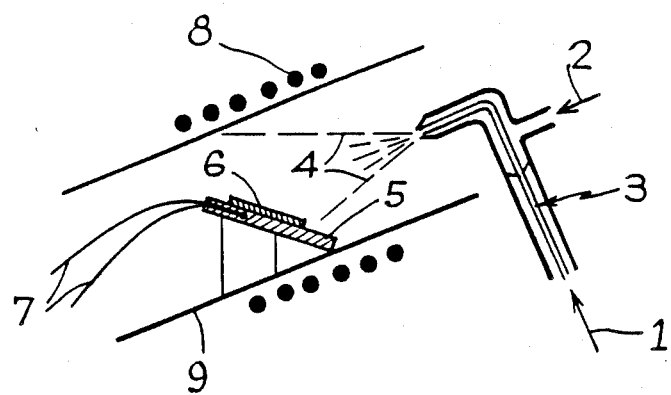

PROCESS FOR MAKING BIOACTIVE COATINGS ON OSSEOUS PROSTHESES, AND PROSTHESES THUS OBTAINED

CROSS REFERENCE

This application is a continuation-in-part of application Ser. No. 626,901, filed July 2, 1984, and now abandoned.

The present invention relates to a process for making bioactive coatings on osseous prostheses and it also relates to the prostheses thus obtained.

In U.S. Pat. No. 4,366,183, a process was described for the making of bioactive coatings on osseous prostheses; this process is characterized by the fact that a mist is made of fine droplets containing calcium ions and orthophosphate ions and said mist is brought into contact with an implant of inert material under conditions such that at least one calcium phosphate is formed by reaction on the hot surface of the said implant.

Said U.S. Pat. No. 4,366,183 specified, firstly, that the implant had to be heated to a temperature between 200° and 600° C. and, secondly, in order to increase the speed of the deposition (that is, the speed of making a deposit of adequate thickness), it was desirable to preheat the mist by passing it through an oven at a temperature between 100° and 300° C. In the examples given in said application, the preheating oven was raised to the temperature of 300° C., 100° C., 200° C., 280° C.

Continuation of work on finalization of the process described in U.S. Pat. No. 4,366,183 allowed determination of the optimal conditions for making deposits. It is plain that the making of deposits under the experimental conditions described allows the making of deposits either in accordance with the technique of a vapor-phase deposit or in accordance with the technique of a liquid-phase deposit; more precisely, the deposits (hence, the phosphates formed on the substrate) can be made on a dry substrate or on a substrate covered with a film of liquid. The examples supplied in U.S. Pat. No. 4,366,183 seem, for reasons associated with the speed of deposition, to advantage the making of said deposits on a dry substrate requiring complete vaporization (or practically complete) of the droplets of liquid that form the mist before said droplets reach the surface of the substrate (or implant).

It has now been found, and this is the purpose of the present application, that the deposits made by the mist technique described in U.S. Pat. No. 4,366,183, could very advantageously be made in the liquid phase, that is by experimental conditions that always provoke a liquid film on the surface of the substrate (or implant) during deposition.

Thanks to said liquid phase deposit, it is possible to obtain more easily and with greater speed, bioactive calcium phosphates allowing a Ca/$p$ ratio higher than about 1.2 (calcium-deficient hydroxyapatites) and good surface qualities.

The present invention relates to a process for making, on osseous prosthesis substrates, bioactive coatings based on calcium-deficient hydroxyapatites having a Ca/$p$ ratio higher than 1.2, said process comprising the steps of forming, from aqueous solutions of dibasic calcium phosphate, a mist of droplets containing calcium ions and orthophosphate ions and bringing said mist into contact with the substrate in an inert material (for example an implant) appropriately heated in such conditions that a thin solid bioactive deposit forms on the substrate from the liquid film, which is formed in situ on said substrate.

The invention process for making bioactive coatings on osseous prostheses substrate comprises the steps of:

(1) placing an osseous prosthesis substrate made of an inert material on a support;

(2) heating said support to between 250° and 500° C.;

(3) atomizing on said substrate a saturated aqueous solution of a dibasic calcium phosphate maintained at a temperature between 5° and 30° C., said solution being carried by air or by an inert atomizing gas under the form of a mist of droplets in such conditions that, for one cm2 of the substrate to be coated, the flow rate of the atomizing gas is higher than 4.5 l/min and the flow rate of the solution is higher than 200 ml/hr.

In the conditions of the invention process, a continuous liquid film forms on the hot substrate from the aqueous solution, the temperature of which is comprised between 55° and 95° C., i.e. at a temperature below its vaporisation temperature. This liquid film remains at a very low distance from the substrate without being instantaneously vaporized due to the steam cushion isolating the cold solution from the hot substrate.

In comparison with the process disclosed in U.S. Pat. No. 4,366,183, the invention process allows the formation of a metastable liquid film which provides:

an excellent mobility of the chemical species (ions)

a better homogeneity of the deposited layers by homogeneity of composition and temperature;

a greater rapidity of the chemical reactions.

Furthermore, it should be noted that the deposit speeds are 5 to 10 times higher and that the crystallinity of the deposit is much improved.

Finally, the homogeneity of the deposit is obtained on several cm2 whereas without liquid film said homogeneity is optimal only on a few mm2.

According to the invention process it is possible to obtain a deposit of around 5 $\mu$m for one hour.

The use of the invention process is simpler than the one of the process disclosed in U.S. Pat. No. 4,366,183, since it is not necessary to preheat the mist of droplets. On the other hand, the droplets can be formed conventionally by an air pneumatic atomizer, by which the said droplets are atomized directly onto the surface of the substrate to be coated.

A consequence of the non-pre-heating of the liquid droplets and the fact that the water must be evaporated on the surface of the substrate, is that said substrate must be energetically heated (in other words, a sufficient quantity of heat must be added per unit of time). It has been found, and this constitutes another aspect of the present invention, that it is very advantageous to heat said substrate by a method of heating by which the heat is generated in the mass of the said substrate or in an appropriate mass in contact with said substrate such as, for example, heating by infrared rays, by laser or, preferably, by high-frequency induction.

The device used to implement the invention is illustrated on the single drawing that illustrates:

an air pneumatic atomization instrument with a capilary tube 3 at which arrives the solution to be atomized 1, an input 2 for the atomizing gas (compressed air) that produces the spray;

a heating appliance 8 formed of a loop of a high frequency furnace;

the furnace carries a graphite support 5 placed in a reactor 9 made in a heat-resistant material such as silica;

the substrate 6 to be coated is placed on the support 5;

the temperature of the support 5 is controlled by a thermocouple 7;

the jet 4 leaving the pneumatic atomizer is projected directly on the surface of substrate 6.

The following non-limited examples illustrate the invention without limiting the scope thereof.

EXAMPLE 1

Using the device described above, four deposits were made on plates (10 mm×20 mm), holding at 260° C. the temperature of support 5 (thermocouple 7). The experimental conditions are as follows:

TABLE I

| Deposit | 1a | 1b | 1c | 1d |
|---|---|---|---|---|
| Flow rate of atomizing gas (air) (1/min.) | 7.3 | 8.2 | 9 | 9.8 |
| Liquid film on substrate | none | thick | average | light |
| Flow rate of solution atomized (ml/h) | 300 | 800 | 600 | 400 |
| Pressure of atomizing gas (kg/cm$^2$) | 1.5 | 2 | 2 | 2 |

The deposits obtained have been analyzed to determine their composition; notably, it was found that the Ca/P ratio was 1.05±0.05 in conditions 1a, 1.25±0.05 in conditions 1b, and 1.20±0.02 in conditions 1c and 1d.

It therefore appears that the composition of the deposits is significantly the same, whatever the thickness of the liquid film, but that said composition is distinctly different when there is no liquid film.

Complementary tests have shown that the quality of the deposits obtained with the liquid film was higher than that of the deposits obtained with no liquid film.

EXAMPLE 2

An attempt was made in this example to determine the importance of the temperature according to the invention process. It was first designed for the purpose of finding the ratio between temperature measured in the graphite support 5 (measured by thermocouple 7) and that measured in the liquid film, all other factors being equal.

| Temperature in 5 | Temperature in liquid film |
|---|---|
| 250 | 55 |
| 300 | 70 |
| 340 | 80 |
| 400 | 85 |
| 450 | 90 |
| 500 | 95 |

A number of tests were then carried out under the following experimental conditions (table II):

TABLE II

| Deposit | 2a | 2b | 2c | 2d | 2e | 2f | 2g |
|---|---|---|---|---|---|---|---|
| Temperature T (° C, in 5) | 260 | 300 | 330 | 360 | 380 | 400 | 500 |
| Flow rate of atomizing gas (air) (1/min.) | 9 | 9.6 | 9.6 | 9.6 | 9.8 | 9.8 | 10.6 |
| Flow rate of solution atomized (ml/h) | 600 | 700 | 700 | 740 | 800 | 830 | 950 |
| Pressure of atomizing gas (kg:cm$^2$) | 2.0 | 2.0 | 2.1 | 2.1 | 1.9 | 1.9 | 2.3 |

It was found for all these tests that the deposit was made with a thin layer of liquid on the substrate.

The deposits were analyzed for Ca/$_p$ giving the following value:

2a=1.20, 2b=1.25, 2c=1.28, 2d=1.37, 2e=1.27, 2f=1.38 and 2g=1.35.

Analyses by infrared spectrometry showed :

that deposits 2d, 2f and 2g had the same characteristics as calcium-deficient apatites;

that the other deposits seemed to consist of a mixture of a calcium-deficient apatitic phase and of a bicalcic phosphate phase.

The above experiments were all carried out with an aqueous starting solution containing 120 mg of Ca H P0$_4$, 2H$_2$0, in 1 liter of distilled water and by pneumatically atomizing this solution with air as atomizing gas.

The supports (or substrates) coated with deposits according to this application proved to be particularly advantageous for the making of osseous prostheses (articular prostheses or dental implants, for example) on account of their ability to associate themselves tightly with the osseous materials with which said deposits come in contact.

What is claimed is:

1. Process for making, on osseous prostheses substrates, bioactive coatings based on calcium-deficient hydroxyapatites having a Ca/$_P$ ratio higher than 1.2, said process comprising the steps of forming, from aqueous solutions of dibasic calcium phosphate, a mist of droplets containing calcium ions and orthophosphate ions and bringing said mist into contact with the substrate made in an inert material appropriately heated, said process comprising the steps of:

(1) placing an osseous prosthesis substrate made of an inert material on a support;

(2) heating said support to between 250° and 500° C.;

(3) atomizirgon said substrate a saturated aqueous solution of a dibasic calcium phosphate maintained at a temperature between 5° and 30° C., said solution being carried by air or by an inert atomizing gas under the form of a mist of droplets in such conditions that, for one cm2 of the substrate to be coated, the flow rate of the atomizing gas is higher than 4.5 1/min and the flow rate of the solution is higher than 200 ml/hr.

* * * * *